… … …

United States Patent [19]
Arai et al.

[11] Patent Number: 5,592,290
[45] Date of Patent: Jan. 7, 1997

[54] METHOD FOR CORRECTING INSTRUMENTAL ERROR OF SPECTROSCOPE OF OPTICAL ANALYZER

[75] Inventors: Fuminori Arai; Yoshikazu Amano; Kiyoshi Yamada, all of Asaka, Japan

[73] Assignee: Fuji Photo Film Co., Ltd., Kanagawa, Japan

[21] Appl. No.: 358,486

[22] Filed: Nov. 14, 1994

[30] Foreign Application Priority Data

Nov. 12, 1993 [JP] Japan .................................. 5-307332

[51] Int. Cl.$^6$ .................................................. G01J 3/00
[52] U.S. Cl. .................. 356/300; 356/402; 356/243; 364/571.02; 364/571.05
[58] Field of Search ........................ 356/300, 319, 356/445–448, 323, 325, 326, 328, 418, 243, 402, 309, 346, 434–435, 32–35, 35.5, 431, 436; 364/497–498, 571.01–571.08, 526, 525, 558, 572–582; 436/43, 47, 164; 422/63–67; 250/363.09; 73/1 R

[56] References Cited

U.S. PATENT DOCUMENTS

| | | | |
|---|---|---|---|
| 4,729,657 | 3/1988 | Cooper et al. | 356/319 |
| 4,832,488 | 5/1989 | Hirai et al. | 356/243 |
| 4,884,213 | 11/1989 | Iwata et al. | 364/497 |
| 5,016,203 | 5/1991 | Komatsu et al. | 364/571.02 |
| 5,357,336 | 10/1994 | Ruhl, Jr. et al. | 356/402 |

FOREIGN PATENT DOCUMENTS

| | | |
|---|---|---|
| 0212660 | 3/1987 | European Pat. Off. . |
| 0305563 | 3/1987 | European Pat. Off. . |
| 0290013 | 11/1988 | European Pat. Off. . |
| 61-041947 | 2/1986 | Japan . |
| 61-68539 | 4/1986 | Japan . |

*Primary Examiner*—Vincent P. McGraw
*Assistant Examiner*—K. P. Hantis
*Attorney, Agent, or Firm*—McAulay Fisher Nissen Goldberg & Kiel, LLP

[57] ABSTRACT

A method for correcting an instrumental error due to wavelength error of a spectroscope of an optical analyzer for measuring an optical density reflected from or transmitted through a dry analysis element. One standard color plate having a standard optical density $OD_{ST}$ is measured by an optical analyzer to be corrected to obtain an measured value $OD_M$. A measured optical density $OD_S$ of the element applied with a sample through the optical analyzer to be corrected is corrected by using a ratio of $OD_M/OD_{ST}$ to obtain a corrected measured value $OD_C$ of the sample. The standard color plate to be used contains an indicator dye contained in the non-reacted dry analysis element or a dye having an absorption spectrum same as or similar to that of the indicator dye in the measurement wavelength range. Another correction method in consideration of a layer coefficient of a dry analysis element is also provided.

6 Claims, 2 Drawing Sheets

METHOD FOR CORRECTING INSTRUMENTAL ERROR OF SPECTROSCOPE OF OPTICAL ANALYZER

BACKGROUND OF THE INVENTION

1. Field of the Invention

The present invention relates to a method for correcting an instrumental error, mainly due to a wavelength error of a spectroscope or spectrometer which is provided with or built in an optical analyzer for measuring a content, a concentration or an activity of an analyte by measuring an optical transmitting or reflection density of a dry analysis element.

2. Description of the Related Art

The dry analysis element is an analysis element which comprises one or plural functional layers and an analytical reagent composition is contained in at least one (or plural) of these functional layers so as to form a coloring dye by the reaction taking place in the layer. The thus formed dye is colorimetrically analyzed by measuring the transmitting or reflection light from the outside of the analysis element. Since such a dry analysis element is stored and preserved in the dry state prior to the analysis operation, there is no need for preparing the reagent at the measuring step. Furthermore, since the reagent has a higher stability in the dry condition, the process using such a dry analysis element is improved in simplicity and quickness of operation over the conventional wet process in which the reagent solution should be prepared as required. The dry process or method using the dry analysis elements has become rapidly a popular analytical method which can easily realize an automated analyzing system in the field of clinical examinations where a number of test samples are to be handled as routine works.

For a quantitative analysis, a liquid solution containing the analyte is spotted or applied onto the dry analysis element and an optical density of a transmitting light through or a reflected light from the analysis element after the completion of the coloring reaction is measured by optical density measuring instruments such as a colorimeter and a spectrophotometer. In such a method, generally, it is common practice to determine the content of the analyte by using a standard curve (commonly referred to as "calibration curve") which has been preliminary drawn by plotting the interrelation between the known contents of the analyte in the standard samples and the optical transmitting or reflection densities of the analysis elements to which standard samples are applied.

However, there is a problem such that an instrumental error is caused due to variation or deviation of the optical density measuring apparatus as used. That is, even when analysis elements of the same manufacturing lot are used, measured values obtained by different optical analyzer may be fluctuated. The optical density measuring apparatus spectroscopically divides the irradiating light or the measuring light through spectroscopes such as a diffraction grating or an interference filter into a monochromatic light of specified wavelength, and is used to measure the optical density of light at the specified wavelength. The accuracy of measurement depends on the performance (accuracy of the spectral centroid of the measured central wavelength, spectral band width and peak width at half height of the spectrum) of the spectroscope. Particularly, the interference filter type spectrophotometer has no adjustability of the spectral centroid and spectral band width of measured light, therefore, the performance of this spectroscope is a cause of the instrumental error. When the absorption wavelength spectrum of a subject to be measured, i.e., the formed dye produced in the analysis element, is relatively moderate pattern and the optical density at the wavelength peak (or trough) of this spectrum is to be measured, a slight error of the measured wavelength and the half-amplitude level hardly affects the measurement value (optical density) obtained and the instrumental error cannot be a serious problem. However, if a slope portion of the absorption wavelength spectrum of the subject to be measured is the wavelength to be spectrophotometrically measured, a measurement value (optical density value) to be obtained fluctuates even with a slight deviation of the measured central wavelength and the half-amplitude level, and therefore the error or difference between measuring instruments cannot be ignored.

Therefore, in most cases, the standard or calibration curve is prepared for each measurement and each measuring apparatus to ensure the accuracy of quantitative analyses. However, a number of standard samples must be prepared and examined to draw a standard curve, it is troublesome to prepare these standard samples for each assay, and the quickness of analyses is impaired.

To avoid the complexity of such drawing of the standard curve for each analysis, a few method has been proposed wherein a sample having known content or concentration is measured by the measuring apparatus to detect an error or difference of the measurement so that the instrumental error of the measuring apparatus is corrected or compensated. For example, the instrumental error correcting method for the optical density measuring apparatus which uses a correction or compensation plate (the standard colored plate) has been proposed in the Unexamined Japanese Patent Publication No. 60447/1992. In the method disclosed in the Unexamined Japanese Patent Publication No. 60447/1992, a dry analysis element contains either of the same dye as the final product (formed dye) of the measuring system or a colored matter having an absorption spectrum similar to that of the formed dye in the measuring wavelength range, and such dry analysis element is used as a compensation plate or colored standard plate. In details, an optical density ($OD_0$) is obtained by measuring a sample through an interference filter, which is the reference filter, and on the other hand, an optical density value ($OD_x$) is obtained by measuring the same sample through a specific interference filter, which is a target of compensation and then the interrelation between these optical density values is represented as a primary function shown by the following formula (1) and correction coefficients k and j of this correction formula (1) are evaluated.

$$OD_0 = k \times OD_x + j \qquad (1)$$

To obtain these correction coefficients k and j, a plurality of correction plates (standard colored plates) having different optical density values (typically, optical density of a reflected light) are prepared to be measured through both the reference interference filter and a specific interference filter to be compensated, and a primary regression analysis is conducted from the OD values obtained from these filters. Since the correction plates to be used in this method contain the dye or coloring matter having the absorption spectrum as same as or similar to that of the final product (formed dye) in the analysis elements, the method using such a correction plate is more excellent in accuracy of the correction of the measurement values in comparison with the conventional method using monochrome filters as the correction plates.

However, since the correction method disclosed in the Unexamined Japanese Patent Publication No. 60447/1992 uses two variables as correction coefficients, at least two correction plates (standard colored plates) having different optical densities are required to be measured. Further, more correction plates would be required because these correction coefficients are actually evaluated by the primary regression equation. To prepare these correction plates, the final product (formed dye) of the measuring assay system or the dye having a similar absorption spectrum should be contained in advance in the dry analysis element, and therefore such analysis element for use as the correction plates should be prepared, in addition to the dry analysis element for analysis of the analyte. If the final product (formed dye) of the measuring assay system is unstable and is not durable, a colored matter, which has a similar absorption spectrum of the final product (formed dye) within the measuring wavelength range or region, should be separately provided to prepare a suitable correction plate.

Furthermore, it has become to be clarified that the effect of correction is low, when a blank value of the reagent is high, that is, the analysis element which has not reacted before application of the sample solution has high optical density as a background or reagent blank, or when the optical density after the completion of the coloring reaction is low.

SUMMARY OF THE INVENTION

An object of the invention made in view of the above problems is to provide an improved method for correcting an instrumental error of an optical density measuring apparatus which permits to correct a measured value measured by a measuring apparatus or optical analyzer to be corrected with one correction plate.

A more specific object of the invention is to provide an improved method for correcting an instrumental error with a larger effect even in a case that a reagent blank, i.e., an unused fresh dry analysis element has high optical density while a background or a change of coloring density is small.

The aforesaid object of the present invention is achieved by the provision of a method for correcting an instrumental error of a spectroscope provided with an optical analyzer to be used to measure a content, a concentration or an activity of an analyte in a sample solution by measuring an optical density of a dry analysis element to which the sample solution is applied, comprising the steps of:

providing one standard color plate containing a dye same as an indicator dye contained in the dry analysis element to which the sample solution is not applied and in which the coloring reaction of the indicator dye has not yet taken place, or other dye having an absorption spectrum similar to that of said indicator dye at least in a measurement wavelength range; said standard color plate having a specific optical density as a standard optical density ($OD_{ST}$) which is obtained by measuring the standard color plate by using a standard optical analyzer;

measuring said standard color plate by using an optical analyzer to be corrected, thereby obtaining an optical density ($OD_M$);

measuring the dry analysis element to which the sample solution is applied and in which the coloring reaction has taken place by using said optical analyzer to be corrected, thereby obtaining an optical density ($OD_S$) of the sample; and correcting the optical density ($OD_S$) of the sample by using a correction formula of $$OD_C=(OD_{ST}/OD_M) \times OD_S$$

to obtain a corrected optical density ($OD_C$) of the sample.

In the present invention, only one standard color plate is used and the correction coefficient(s) can be obtained from the optical density ($OD_{ST}$) of the standard color plate measured by the standard or reference analyzer and the optical density ($OD_M$) of the standard color plate measured by an incorrected analyzer which should be corrected. Since the optical density (specific optical density) of the standard color plate measured by the standard analyzer can be generally given as a known optical density, a correction coefficient $F=OD_{ST}/OD_M$ can be obtained only by measuring one standard color plate through the incorrected analyzer one time so that the optical density of the analysis element spotted or applied with the sample can be corrected by using thus obtained correction coefficient(s).

For this purpose, the standard color plate may contain a dye same as the indicator dye composition contained in the non-reacted or unused dry analysis element. As this standard color plate, a fresh dry analysis element to which the sample solution is not yet applied by spotting can be directly used. Or a dye in the standard color plate may be the dye having an absorption spectrum same as or similar to the absorption spectrum of the indicator dye contained in the non-reacted dry analysis element at least in the measurement wavelength range so that the standard color plate has a specific optical density at the measured wavelength.

DETAILED DESCRIPTION OF THE INVENTION

Figure 1:
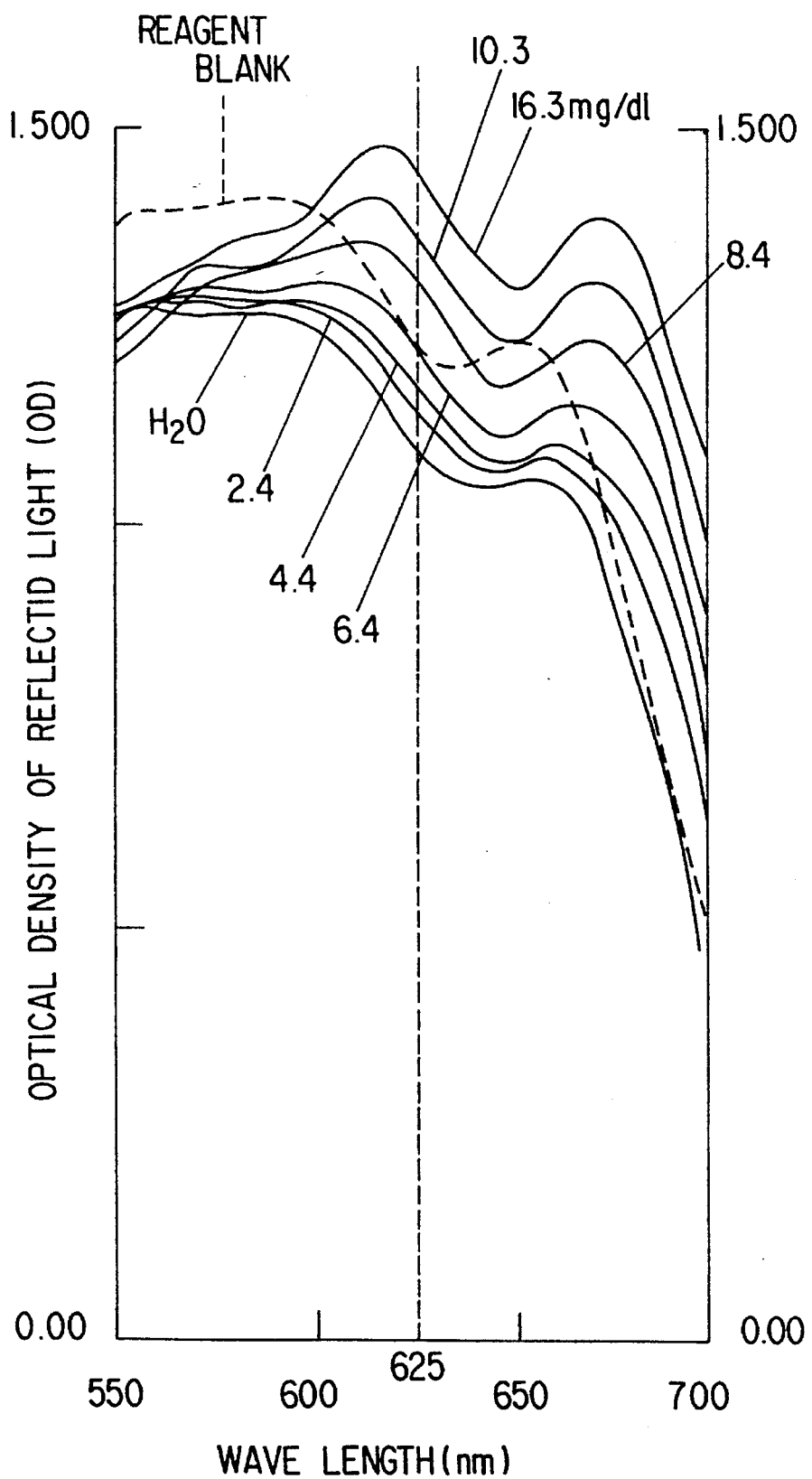
FIG. 1 is a diagram illustrating the principle of the present invention.

In order to correct the measured optical density value having an instrumental error due to the wavelength error or deviation of the incorrected analyzer i.e., the analyzer to be corrected, essentially, it is preferable to measure the optical density of the dry analysis element to which the sample is indeed spotted by a standard optical analyzer and an concerned optical analyzer to be corrected and to conduct correction of the measured values measured by the incorrected analyzer in consideration of the difference of these values. To avoid the troublesomeness of such correction procedure at each measurement, the method disclosed in the Unexamined Japanese Patent Publication No. 60447/1992 uses a dry analysis element as a correction plate (standard color plate), in which the dry analysis element does not contain the non-reacted indicator dye but contains a dye as same as the final product (formed dye) of the measuring system, or the dry analysis element contains the colored matter which has a similar absorption spectrum to the formed dye in the same absorption wavelength range as the measurement wavelength range. However, the present inventor has found that actually such final product (formed dye) of the measuring system is not always required to be added into the standard color plate, and the non-reacted indicator dye can also be used as the coloring matter in the standard color plate for correction. This assumes that it depends on the particular characteristics of the dry analysis element, as described below.

In general, the indicator dye is excessively contained in the dry analysis element as compared with the quantity of the analyte to be actually analyzed, so that it is as much as enough to react with the analyte in the determination range. An excessive quantity of the reagent dye is required, taking the reaction efficiency into account. Therefore, it is usual to include the indicator dye in a quantity as much as several times the required stoichiometric quantity in the dry analysis element. Accordingly, the dry analysis element, after the sample solution has been applied thereto and the coloring reaction of the indicator dye has completed, as still contains a large quantity of non-reacted indicator dye as well as the formed dye. As result, the absorption spectrum presented by the dry analysis element after the sample has been applied thereto is a sum of the absorption spectrum of the formed dye and the absorption spectrum of the remaining non-reacted indicator dye. If a molecular extinction coefficient of the non-reacted indicator dye at the measurement wavelength is sufficiently lower than the molecular extinction coefficient of the formed dye, such non-reacted indicator dye less affects the measured values. This corresponds to the case that the optical density at the measurement wavelength of the reagent blank (fresh dry analysis element to which the sample solution has not yet been spotted) is sufficiently low.

However, if the optical density of the reagent blank is high and the color density after reaction is low (i.e., the S/N ratio is low and the dynamic ratio is low), the absorption spectrum of the non-reacted reagent dye cannot be ignored. In such case, the absorption spectrum of the non-reacted indicator dye substantially contributes to the entire absorption spectrum presented by the dry analysis element after the sample has been spotted thereto, and therefore the absorption spectrum of the dry analysis element after the application of the sample in the measurement wavelength range is similar or closer to the absorption spectrum of the non-reacted indicator dye. In such condition, the inventor has found that even the fresh dry analysis element which contains the non-reacted indicator dye but does not contain the formed dye can be used as the standard color plate for conducting the correction in this case. Moreover, in this case, the optical density of the reagent blank is high and a correction line for correcting the measured value can be approximated to actually pass through the origin of the coordination system so that plural standard color plates having different optical densities need not be prepared and be measured for the correction.

FIG. 1 shows an optical density spectrum of a reflected light obtained when calcium chloride solutions having various concentrations shown with numerical values in FIG. 1 are spotted to the dry analysis element for analyses of calcium chloride used in the working example described hereinafter. The spectrum of the reflected light from the analysis element changes as shown in FIG. 1 as the concentration of the $CaCl_2$ solution increases from 0 (represented as "$H_2O$" in FIG. 1). The measurement wavelength 625 nm for analysis is selected from this variation of the spectrum as a wavelength where the optical density largely changes and the change of the optical density has a linearity. However, this measurement wavelength is not the peak of the spectrum. Consequently, even if the wavelength range to be actually measured is slightly deviated due to the performance of the spectroscope of the measuring apparatus, the optical density value is substantially affected. Meantime, the spectrum of the reflected light of the fresh dry analysis element, that is, the reagent blank to which the sample solution has not yet been applied, is as shown with the broken line in the diagram of FIG. 1. The gradient or slope of the spectrum curve at measurement wavelength of 625 nm is almost same as that when calcium chloride solutions of different concentrations are applied to the analysis element. Under the above condition, analytical measured values obtained by the measuring apparatus to be corrected can be corrected by the formula (2) given below.

$$F = OD_{ST}/ODM$$

$$OD_C = F \times OD_S = (OD_{ST}/OD_M) \times OD_S \quad (2)$$

$OD_{ST}$: Optical density of the reagent blank analysis element measured by the standard analyzer;

$OD_M$: Optical density of the reagent blank analysis element measured by the analyzer to be corrected;

F: Correction coefficient $OD_S$: Optical density of the dry analysis element to which the sample is spotted, measured by the analyzer to be corrected $OD_C$: Corrected optical density A correction method according to the present invention can be practiced in the range of measurement wavelength of 200 nm to 800 nm. The optical density (OD) can be corrected in the range of 0.1 to 2.2, preferably in the range of 0.15 to 2.0. The range of correctable wavelength range is ±40 nm, preferably ±20 nm of the measurement center wavelength of the standard analyzer or measuring apparatus. Since the correctable range depends on the spectrum of the measuring indicator dye, this should be taken into account.

The present correction method exhibits its effects in the measurement system in which the coloring density less changes despite that the value of the reagent blank is high. In details, when the optical density ($OD_B$) of the standard color plate (reagent blank) measured with the measurement wavelength of the spectroscope of the analyzer to be corrected has an interrelation with the optical density ($OD_R$) Of the dry analysis element to which the sample solution containing the analyte within the normal determination range is spotted to take place the coloring reaction, as given below, $$(OD_R - OD_B)/OD_B \leq 0.7$$

the present correction method exhibits excellent correction effects.

Even in the case of the relationship between $OD_R$ and $OD_B$ as given below, $$0.7 < (OD_R - OD_B)/OD_B \leq 1.0$$

the correction effect is observed and the present correction method can be applied but, if the value of $(OD_R - OD_B)/OD_B$ exceeds 1.0, this correction method is unsuitable.

If a standard color plate containing a dye similar to the indicator dye contained in the reagent blank, instead of the reagent blank, is used as the standard color plate, such standard color plate may be composed of layer structures same as the usual dry analysis element, except that the layer, which should contain the indicator dye for the usual dry analysis element, may contain a dye or coloring matter having an absorption spectrum same as or similar to that of the indicator dye within the measurement wavelength range, in lieu of the indicator dye.

In such case, the measurement wavelength range refers to a range of wavelength of the central wavelength ($\lambda 0$) $\pm 5$ nm of the spectroscope of the standard analyzer. The words "the absorption spectrum is similar to" means that there is a relationship between a mean gradient or slope ($C_T$) of a reflection spectrum of the indicator dye contained in the non-reacted dry analysis element and a mean gradient ($S_T$) of a reflection spectrum of a dye (or an indicator dye) contained in the standard color plate is in a relationship as given below:

$$0.5 \times S_T \leqq C_T \leqq 2.0 \times S_T \text{ when } C_T \geqq 0 \text{ and } S_T \geqq 0$$

or $$0.5 \times S_T \leqq C_T \geqq 2.0 \times S_T \text{ when } C_T < 0 \text{ and } S_T < 0$$

Preferably, the relationship is given below:

$$0.7 \times S_T \leqq C_T \leqq 1.5 \times S_T \text{ when } C_T \geqq 0 \text{ and } S_T \geqq 0$$

or $$0.7 \times S_T \geqq C_T \geqq 1.5 \times S_T \text{ when } C_T < 0 \text{ and } S_T < 0)$$

The dye (or the indicator dye) contained in the standard color plate and having above-described relationship is referred to as a dye (or an indicator dye) which has a similar absorption spectrum. The mean gradient of the reflection spectrum means an arithmetic mean value of gradient values (11 values) of the reflection spectrum obtained at every nm of wavelength in the measurement wavelength range.

Since the correction coefficient to be obtained in this instrumental error correction method is only one coefficient or factor F, the correction coefficient F can be normally obtained by measuring the reagent blank at only one point. However, if the reagent blanks (that is, fresh dry analysis elements) of plural lots having different optical densities can be prepared, the correction coefficient F may be obtained in the primary regression correlation from the optical densities ($OD_S$) of a plurality of reagent blanks.

In a case that the dry analysis element of the reagent blank is stable and the optical density $OD_{ST}$ of the reagent blank measured by the standard analyzer is not fluctuated, such optical density may be stored in the measuring apparatus or analyzer to be corrected as a predetermined value, and thereby the correction coefficient F can be more quickly calculated to correct the measured value of the sample at the time of analysis. In the case that the reagent in the dry analysis element is unstable and its optical density varies during storage, this correction method is originally unpreferable for the measuring system. Even in such case, however, the correction coefficient F can be obtained by simultaneously measuring the reagent blank in the standard analyzer and the measuring analyzer to be corrected. Generally, however, the original object of the dry analysis element is to manufacture stable reagent blanks (i.e., the dry analysis element before use) so that a time-elapsed change of the dry analysis element due to storage and custody is minimized and therefore the reagent blanks are stable in many measurements of the dry analysis element.

It is preferable to obtain the correction coefficient F in each measurement, however, such practice will be heavy loads for operators. If the optical system of the measuring apparatus to be corrected less fluctuates, once the correction coefficient F is obtained for such measuring apparatus, thus obtained coefficient F may be stored in the same measuring apparatus so as to omit evaluation processes of coefficient F at next or future every measurement for this measuring apparatus.

The object of the present invention is also attained by a method for correcting an instrumental error of a spectroscope provided with an optical analyzer to be used to measure a content, a concentration or an activity of an analyte in a sample solution by measuring an optical density of a dry analysis element to which the sample solution is applied, comprising the steps of:

providing one standard color plate which contains one of following dyes, a) a dye same as an indicator dye contained in the dry analysis element to be used for analysis of the analyte;

b) a dye having an absorption spectrum substantially same as or similar to an absorption spectrum of the indicator dye in a measurement wavelength range; and c) a dye having an absorption spectrum substantially same as or similar to an absorption spectrum of a formed dye in the measurement wavelength, the formed dye being formed by coloring reaction of the indicator dye in the presence of the analyte;

said standard color plate having a specific optical density as a standard optical density ($OD_{ST}$) which is obtained by measuring the standard color plate by using a standard optical analyzer;

measuring said standard color plate by using an optical analyzer to be corrected, thereby obtaining an optical density ($OD_M$);

measuring the dry analysis element to which the sample solution is applied and in which the coloring reaction has taken place by using said optical analyzer to be corrected, thereby obtaining an optical density ($OD_S$) of the sample;

determining an instrumental error correction coefficient gradient ($\Phi$) of wavelength and an instrumental error correction coefficient intercept ($\Lambda$) by using these measured values ($OD_{ST}$ and $OD_M$) and a layer coefficient (L: constant value), which is predetermined from a layer structure of the dry analysis element, as given below;

$$\Phi = (OD_{ST} - L)/(OD_M - L)$$

$$\Lambda = [(OD_M - OD_{ST})/(OD_M - L)] \times L$$

and correcting the optical density ($OD_S$) of the sample by using a correction formula of $$\begin{aligned} OD_C &= \Phi \times OD_S + \Lambda \\ &= [(OD_{ST} - L)/(OD_M - L)] \times OD_S + \\ &\quad [(OD_M - OD_{ST})/(OD_M - L)] \times L \end{aligned}$$

to obtain a corrected optical density $OD_C$ of the sample.

In measurement of the reflection optical density of the dry analysis element, the optical density of the reflected light may vary depending on the layer structure of the dry analysis element. For example, if a layer containing barium sulfate or titanium dioxide is provided in the layer structure to make it function as a light reflection layer or a light shielding layer, the reflection optical density of the analysis element lowers. The optical density can be corrected by using the values $OD_{ST}'(=OD_{ST}-L)$, $OD_M'(=OD_M-L)$ and $OD_S'(=OD_S-L)$ obtained by subtracting a specific coefficient (layer coefficient L), which is determined according to such layer structure, from respective apparent optical density values $OD_{ST}$, $OD_M$ and $OD_S$. In this case, the correction formula (3) will be described as given below.

$$F=OD_{ST}'/OD_M'=(OD_{ST}-L)/(OD_M-L) \quad OD_C'=OD_C-L \quad OD_C'=F \times OD_S' \quad OD_S'=(OD_{ST}'/OD_M') \times OD_S' \quad OD_C-L=F \times (OD_S-L) \quad (3)$$

$OD_{ST}$: Optical density of the reagent blank analysis element measured by the standard analyzer.

$OD_M$: Optical density of the reagent blank analysis element measured by the analyzer to be corrected.

F: Correction coefficient $OD_S$: Optical density obtained from the analyzer to be corrected with respect to the dry analysis element to which the sample was spotted and in which the coloring reaction completed.

$OD_C$: Corrected optical density

L: Layer coefficient (constant value)

From the formula (3), the corrected value $OD_C$ can be shown as the formula (4) given below:

$$\begin{aligned} OD_C &= F \times (OD_S - L) + L \quad (4) \\ &= [(OD_{ST} - L)/(OD_M - L)] \times (OD_S - L) + L \\ &= [(OD_{ST} - L)/(OD_M - L)] \times OD_S + \\ &\quad [(OD_M - OD_{ST})/(OD_M - L)] \times L \end{aligned}$$

For directly calculating the corrected optical density measured value ($OD_C$) of the sample from the optical density measured value ($OD_S$) in the analyzer, it is convenient to calculate the corrected optical density $OD_C$ by using the coordinates of $OD_S$ and $OD_C$ as shown by the formula (4). Accordingly, the formula (5) is defined as given below;

$$\Phi=(OD_{ST}-L)/(OD_M-L)$$

$$\Lambda=[(OD_M-OD_{ST})/(OD_M-L)] \times L \quad (5)$$

Figure 2:
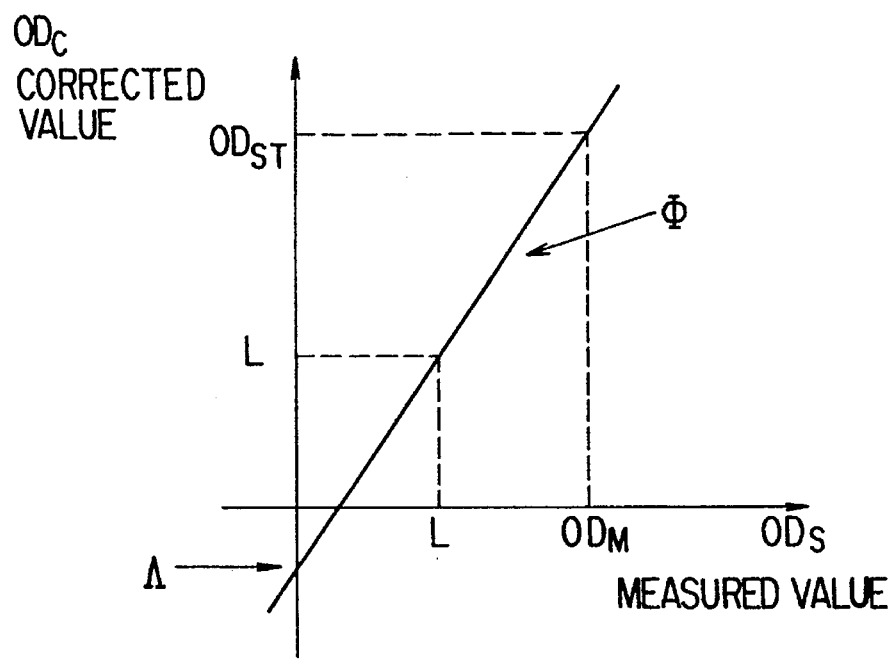
FIG. 2 is a diagram illustrating the principle of the present invention in a case that the layer coefficient L is taken into account.

$\Phi$ represents a gradient of a correction function shown in FIG. 2 (gradient of the wavelength instrumental error correction coefficient) and $\Lambda$ represents an intercept of the same correction function (intercept of the wavelength instrumental error correction coefficient). In other words, as shown in FIG. 2, the correction function determined by the formula (4) can be primarily obtained by plotting the points which are determined according to the optical density $OD_{ST}$ of the standard color plate in the standard analyzer and the optical density $OD_M$ in the incorrected analyzer (analyzer to be corrected).

When the layer coefficient L is far lower than the optical densities ($OD_{ST}$ and $OD_M$) of the reagent blank, for example, as shown below, $$L/OD_{ST} \leq 0.1 \text{ or } L/OD_M \leq 0.1$$

the gradient $\Phi$ of the correction function can be as given below with $L \approx 0$ as an approximate value:

$$\Phi=(OD_{ST}-L)/(OD_M-L) \approx OD_{ST}/OD_M$$

Since a difference (instrumental error) is generally not so larger than the absolute value of optical density ($OD_{ST}$, $OD_M$) of the reagent blank, the optical density can be approximated as $OD_M \approx OD_{ST}$ in most cases, where the $\Lambda$ value A can be approximated to a value given below.

$$\Lambda=[(OD_M-OD_{ST})/(OD_M-L)] \times L \approx 0$$

In this case, the correction formula is as same as shown with the formula (2).

The layer coefficient L is depending on component materials of the dry analysis element and can be assumed as a constant value peculiar to the layer structure which is empirically known. This value L can be obtained by measuring an optical density of the dry analysis element, which is made without containing only the indicator dye, as dry state. In view of this layer coefficient L, the wavelength characteristics to be obtained from the standard color plate used in the present invention are now explained, referring to FIG. 3.

An optical density is assumed as P, when the dry analysis element M to which a sample containing an analyte within the quantitative determination range is spotted is measured by the standard analyzer with the measurement center wavelength $\lambda$. This measured value ($OD_M$) of the optical density P shows the same value P as 25 a corrected value ($OD_C$) which must be shown by the standard analyzer. In the case that the absorption spectrum of the dry analysis element M to which the sample is spotted has a slope or region in the wavelength measuring region, when the measurement center wavelength of the analyzer to be corrected is deviated only as much as $d\lambda$ as compared with the standard analyzer, the measured value of the optical density through the incorrected analyzer deviates as much as dP so as to be P+dP. To correct the measured value (P+dP) obtained by the incorrected analyzer to a corrected value P, which must be shown by the standard analyzer, it is necessary to preset a correction curve or line such as the line B shown in FIG. 3. Therefore, if the standard color plate N is adapted to provide a measured value Q+dQ which is deviated only by dQ in reference to the measured value Q in the standard analyzer, the correction line B for correcting the measured value Q+dQ to the corrected value Q can be obtained. In this case, the layer coefficient L can be an approximately fixed or constant value regardless of deviation of the wavelength and is a fixed point on FIG. 3. Accordingly, the standard color plate N necessary for obtaining the correction function B need to have a wavelength characteristic which provides $dQ=[(Q-L)/(P-L)]\times dP$ for the wavelength deviation $d\lambda$. In other words, an ideal correction can be attained when a slope ($dQ/d\lambda$) at the measurement wavelength of the standard color plate is in a relationship to a slope ($dP/d\lambda$) at the measurement wavelength of the spectrum shown by the dry analysis element to which the sample with the normal quantitative determination range is spotted, as following formula (6).

$$dQ/d\lambda=[(Q-L)/(P-L)]\times(dP/d\lambda) \quad (6)$$

Figure 3:
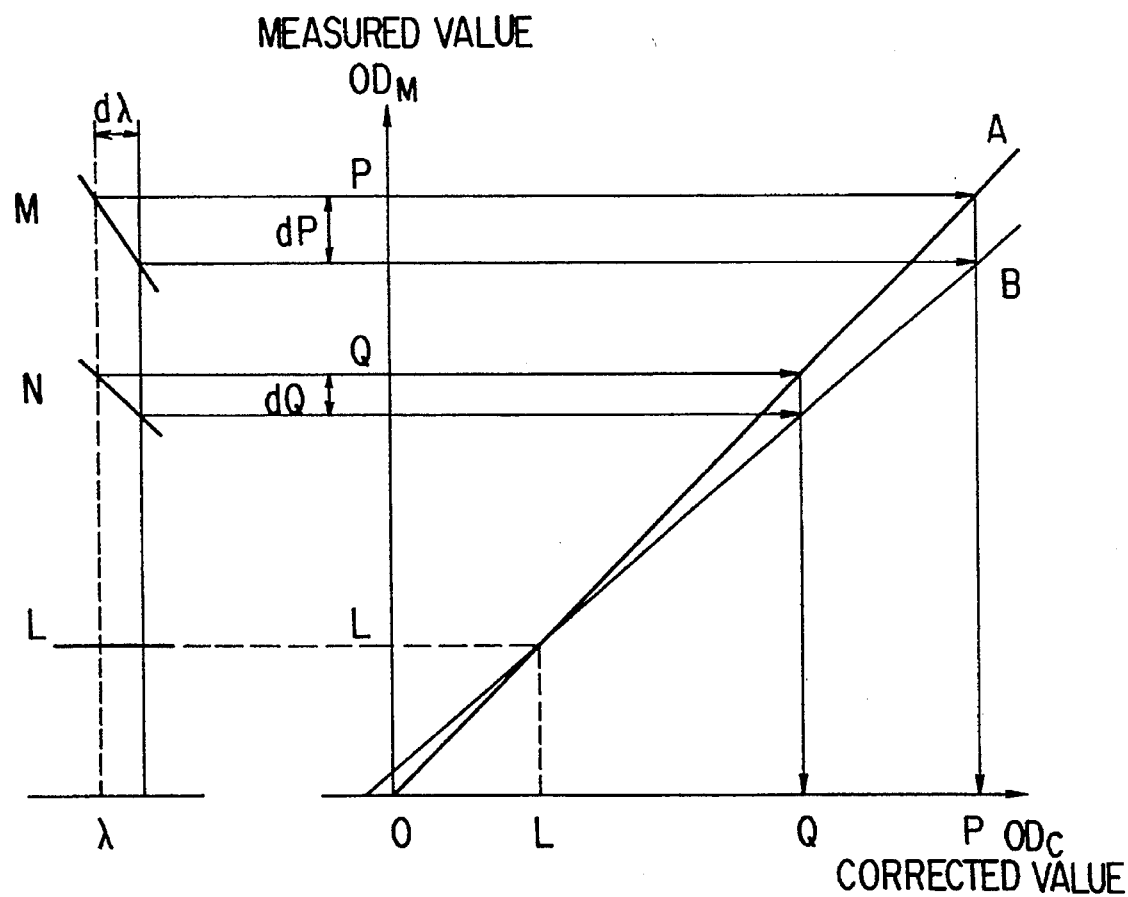
FIG. 3 is an illustration of the wavelength characteristics of the standard color plate according to the present invention in a case that the layer coefficient L is taken into account.

The wavelength gradient ($dQ/d\lambda$) of the standard color plate, if dQ is within the range of 0 to dQ in FIG. 3, is closer to a value $OD_C$ which must be rather shown by the standard analyzer than in a case that correction is not carried out. Therefore, if the relationship represented by the following formula (7) is satisfied, when $dP<0$, $$0>dQ/d\lambda \geq [(Q-L)/(P-L)]\times(dP/d\lambda)$$

when $dP>0$, $$0<dQ/d\lambda \geq [(Q-L)/(P-L)]\times(dP/d\lambda) \quad (7)$$

the correction which permits approximation to the true value can be carried out. If the layer coefficient L is sufficiently small and can be approximate to zero as L≈0, the formula (7) can be approximated as given below:

when dP<0, $$0 > dQ/d\lambda \geq (Q/L) \times (dP/d\lambda)$$

when dP>0, $$0 < dQ/d\lambda \leq (Q/L) \times (dP/d\lambda) \qquad (8)$$

The correction method of the present invention is applicable if the standard color plate which provides the relationship as described above is used.

In the case that the optical density of the reagent blank is high and the coloring density after reaction is relatively low (that is, the S/N ratio and the dynamic ratio are low), the non-reacted indicator dye greatly contributes to the absorption spectrum gradient. Therefore, in addition to the formed dye formed by the coloring reaction of the indicator in the presence of the analyte, the following dye which has the same or similar absorption spectrum to substantially satisfy the relationship described above in the measurement wavelength range can be used in the standard color plate according to the present invention (a) an indicator dye contained in the dry analysis element which is not reacted with the analyte, or (b) a dye which has an absorption spectrum in the measurement wavelength range as same as or similar to the absorption spectrum of the indicator dye contained in the dry analysis element which is not used and not reacted with the analyte.

EXAMPLES

The effects of the correction method according to the present invention were ascertained with respect to fifteen sets of FUJI DRI-CHEM 5000 analyzers (manufactured by Fuji Photo Film Co., Ltd.) each being provided with an optical density measuring apparatus (optical analyzer) having an interference filter spectroscope. The dry analysis element used was prepared in the same method for the slide for calcium analysis in Embodiment 1 disclosed in the Japanese Patent Application No. 26081/1991 (which has been published as the Unexamined Japanese Patent Publication No. 50976/1994).

On a smooth film sheet (support) of colorless and transparent polyethylene terephthalate (PET) having a thickness of 175 μm, coated was an aqueous solution of the following composition, followed by drying to form a reagent layer so that respective components had the coverage as set forth below.

| | |
|---|---|
| Gelatin (purified after alkaline treatment and deionizing) | 12.6 g/m² |
| p-nonylphenoxypolyglycidol (Unit of glycidol: averagely 10 contained) | 350 mg/m² |
| MES (2-(N-Morpholino)ethanesulfonic acid) | 1.96 g/m² |
| Chlorophosphonazor III | 5.33 g/m² |
| Rutile-type titanium dioxide (Chemical Abstracts Registry No. 1914-99-4) | 1.15 g/m² |
| KOH | 1.4 mg/m² |

An aqueous solution containing 1% of a gelatin hardening agent and 0.25% of p-nonylphenoxy polyglycidol was applied onto this reagent layer in the amount of application of 37.6 g/m², and immediately thereafter a tricot knitted cloth made by knitting polyethylene terephthalate spun yarn in which the content of calcium was reduced by a treatment disclosed in the Japanese Patent Application No. 25061/1989 was laminated and adhered thereon, by slightly pressing uniformly the cloth to form a spreading layer.

A following reagent compound was applied onto this reagent layer, followed by drying, and then this layered element was placed set in the mount described in the Unexamined Japanese Patent Publication No. 63452/1982 to prepare an integrated multi-layered analysis element for the analysis of calcium analysis.

| | |
|---|---|
| Polyvinylpyrrolidone (average molecular weight: approx. 120 mil.) | 5 g/m² |
| Nonylphenoxypolyethoxiethanol (Unit of oxyethylene: averagely 10 contained) | 1.25 g/m² |

Measurement Example 1

The following tests were conducted to know the correcting effects when the correction was carried out in each measurement. With a fresh or unused slide of the calcium analysis element obtained as described above as the standard color plate, a reflection optical density $OD_M$ at the wavelength of 625 nm was measured by the measuring apparatus No. 1 of FUJI DRI-CHEM 5000 analyzer as an incorrected analyzer to obtain a mesured optical density $OD_M$ Of the standard color plate measured by incorrected analyzer. Similarly, the reflection optical density ($OD_{ST}$) was measured with the same standard color plate by one set of FUJI DRI-CHEM 5000 analyzer which is referred as the standard or reference analyzer so as to obtain the standard optical density $OD_{ST}$ of the standard color plate. The correction coefficient $F=OD_{ST}/OD_M$ of the measuring apparatus No.I was calculated from the above result.

A human serum of the normal concentration range was supplied by spotting to the slide used as the standard color plate, followed by incubating for four minutes. Then the optical density of the reflected light having a center wavelength of 625 nm was measured and to obtain the reflection optical density ($OD_S$) of the sample. The measured value $OD_S$ was corrected by multiplying it by the correction coefficient F previously obtained so as to obtain $OD_S \times F = OD_C$. Using the thus obtained optical density ($OD_C$) of the sample, the concentration of calcium chloride in the sample was calculated according to the calibration curve separately obtained with the human serum. The results are as shown in the line for the measuring apparatus No. 1 in Table 1. The layer coefficient L of the calcium analysis element used in this case is 0 (zero).

Quite similarly, the fresh slides of different calcium analysis elements was measured by other measuring apparatuses No. 2 to 15 to obtain the measured value ($OD_M$) of the reagent blank respectively and the standard optical density ($OD_{ST}$) was measured by the standard analyzer. Then, human serum sample same as that used for the above measuring apparatus No. 1 was spotted on each of the slides to measure the optical density ($OD_S$) of the sample by each of the measuring apparatus Nos. 2 to 15. Subsequently, in the same manner as the case of the measuring apparatus No. 1, the correction coefficient F for respective measuring apparatuses was obtained, and then the reflection optical density ($OD_S$) of the sample at the respective measuring apparatus was corrected using obtained coefficient F, and finally the value $OD_C$ of the sample and further the calcium concentration were calculated. The results are as shown in the line for the measuring apparatuses Nos. 2 to 15 in Table 1. The measured value ($OD_S$) of the sample obtained from the standard analyzer and the substance concentration are shown in the line of the standard analyzer. The substance concentration value obtained from the standard analyzer shown in this case is a value measured by the standard analyzer provided with the interference filter verified at 625 nm with the standard working curve which is made so that the concentration value coincides with the measured value (verified value) obtained by the wet type calcium standard measuring method which uses a reagent o-CPC (orthocresolphthalein complexon).

apparatus Nos. 1 to 15. With a fresh slide of the calcium analysis element obtained as described above as the standard plate, the reflection optical density ($OD_{ST}$) was measured by one FUJI DRI-CHEM 5000 analyzer as the standard analyzer. The $OD_{ST}$ value was 1.504 as shown in Table 2. The same fresh slide, i.e., standard color plate was measured by 15 sets of measuring apparatuses to be corrected so as to obtain the reflection optical density $OD_M$ for each of the measuring apparatus Nos. 1–15. From these results, the correction coefficient $F=OD_{ST}/OD_M$ of 15 sets of measuring apparatuses was calculated respectively. After spotting of human serum sample to another fresh slide (belonging to the same production lot), followed by incubation for four minutes, the reflection optical density at 625 nm was measured

TABLE 1

| Measuring apparatus | Reagent blank value | | Correction coefficient F | Measured value of sample | | Substance concentration (mg/dL) |
|---|---|---|---|---|---|---|
| | $OD_{ST}$ (standard analyzer) | $OD_M$ (measuring analyzer) | | $OD_S$ Before Correction | $OD_C$ After Correction | |
| Standard | 1.463 | — | — | 1.339 | — | 10.7 |
| 1 | 1.466 | 1.4616 | 1.003 | 1.331 | 1.335 | 10.5 |
| 2 | 1.467 | 1.4424 | 1.017 | 1.308 | 1.330 | 10.2 |
| 3 | 1.459 | 1.4619 | 0.998 | 1.342 | 1.339 | 10.7 |
| 4 | 1.465 | 1.4738 | 0.994 | 1.350 | 1.342 | 10.9 |
| 5 | 1.457 | 1.4599 | 0.998 | 1.339 | 1.336 | 10.5 |
| 6 | 1.453 | 1.4457 | 1.005 | 1.329 | 1.336 | 10.5 |
| 7 | 1.466 | 1.4543 | 1.008 | 1.332 | 1.343 | 10.9 |
| 8 | 1.463 | 1.4630 | 1.000 | 1.339 | 1.339 | 10.7 |
| 9 | 1.466 | 1.4793 | 0.991 | 1.351 | 1.339 | 10.7 |
| 10 | 1.469 | 1.4737 | 0.997 | 1.346 | 1.342 | 10.9 |
| 11 | 1.466 | 1.4500 | 1.011 | 1.323 | 1.338 | 10.6 |
| 12 | 1.465 | 1.4650 | 1.000 | 1.341 | 1.341 | 10.8 |
| 13 | 1.464 | 1.4509 | 1.009 | 1.327 | 1.339 | 10.7 |
| 14 | 1.466 | 1.4558 | 1.007 | 1.325 | 1.334 | 10.4 |
| 15 | 1.458 | 1.4565 | 1.001 | 1.340 | 1.341 | 10.8 |
| | | Mean value of 15 apparatuses | | 1.3348 | 1.3382 | 10.653 |
| | | | SD | 0.0114 | 0.0035 | 0.2030 |
| | | | CV | 0.8592 | 0.2641 | 0.9061 |

As understood from Table 1, the sample measured values obtained from respective measuring apparatuses were corrected to be closer to or approximated to the sample measured values of the standard analyzer. Variations of the sample measured values were reduced from the standard deviation of 0.0114 before correction to the standard deviation of 0.0035 after correction, thereby indicating that the correction method according to the present invention is effective.

Measurement Example 2

The following tests were conducted to examine the effects of correction in the case that the correction was carried out using one standard color plate with respect to the measuring to obtain the reflection optical densities ($OD_S$) of the sample in the measuring apparatuses. The measured value $OD_S$ obtained was corrected by multiplying it with the correction coefficient F obtained as the above-described, thereby the corrected optical density $OD_C$ ($=OD_S \times F$) was obtained. Using thus obtained corrected optical density $OD_C$ of the sample, The calcium concentration of the sample was calculated with referring the standard curve preliminary drawn. These measurements and calculations were carried out with each of 15 sets of measuring apparatuses. The results are shown in Table 2.

TABLE 2

| Measuring apparatus | Reagent blank value | | Correction coefficient F | Measured value of sample | | Substance concentration (mg/dL) |
|---|---|---|---|---|---|---|
| | $OD_{ST}$ (standard analyzer) | $OD_M$ (measuring analyzer) | | $OD_S$ Before Correction | $OD_C$ After Correction | |
| Standard | 1.504 | — | — | 1.339 | — | 10.6 |
| 1 | 1.504 | 1.501 | 1.002 | 1.331 | 1.334 | 10.4 |
| 2 | 1.504 | 1.478 | 1.018 | 1.308 | 1.332 | 10.3 |

TABLE 2-continued

| Measuring apparatus | Reagent blank value | | | Measured value of sample | | Substance concentration (mg/dL) |
|---|---|---|---|---|---|---|
| | $OD_{ST}$ (standard analyzer) | $OD_M$ (measuring analyzer) | Correction coefficient F | $OD_S$ Before Correction | $OD_C$ After Correction | |
| 3 | 1.504 | 1.512 | 0.995 | 1.342 | 1.335 | 10.5 |
| 4 | 1.504 | 1.515 | 0.993 | 1.350 | 1.341 | 10.8 |
| 5 | 1.504 | 1.509 | 0.997 | 1.339 | 1.335 | 10.5 |
| 6 | 1.504 | 1.496 | 1.005 | 1.329 | 1.336 | 10.5 |
| 7 | 1.504 | 1.493 | 1.007 | 1.332 | 1.341 | 10.8 |
| 8 | 1.504 | 1.504 | 1.000 | 1.339 | 1.339 | 10.6 |
| 9 | 1.504 | 1.519 | 0.990 | 1.351 | 1.337 | 10.6 |
| 10 | 1.504 | 1.509 | 0.997 | 1.346 | 1.342 | 10.9 |
| 11 | 1.504 | 1.486 | 1.012 | 1.323 | 1.339 | 10.7 |
| 12 | 1.504 | 1.504 | 1.000 | 1.341 | 1.341 | 10.8 |
| 13 | 1.504 | 1.487 | 1.101 | 1.327 | 1.342 | 10.9 |
| 14 | 1.504 | 1.491 | 1.009 | 1.325 | 1.337 | 10.6 |
| 15 | 1.504 | 1.501 | 1.002 | 1.340 | 1.343 | 10.9 |
| | | Mean value of 15 apparatuses | | 1.3348 | 1.3382 | 10.66 |
| | | | SD | 0.0114 | 0.0033 | 0.1919 |
| | | | CV | 0.8592 | 0.2533 | 1.8009 |

As understood from Table 2, the measured values of the sample obtained from respective measuring apparatuses were corrected to be closer or approximated to the measured value of the sample obtained by the standard analyzer. Variations of the measured values of the sample obtained by respective measuring apparatuses were reduced from the standard deviation (SD) of 0.0114 before the correction to the standard deviation (SD) of 0.0033 after the correction, thereby indicating that the correction method according to the present invention is effective when the same standard color plate is used. This means that, if the optical density of the single standard color plate is in advance measured by the standard analyzer and thus obtained optical density is stored as a known density in the measuring apparatus, such standard color plate is not required to be measured again by the standard analyzer at each measurement.

For examples, the known optical density of the standard color plate may be provided as a magnetic data memorized in a magnetic card so that the magnetic data may be input and stored in the analyzer to be corrected. Also, an optical data such as a bar code data containing such known optical density of the standard color plate may be used for this purpose. Further, such data of known optical density may be provided by the written and readable numerical data attached on of the package of the analysis element to be delivered to the customer, so that the operator can input such numerical data into the analyzer through a keyboard or an optical characters reader or the like.

As described above, the correction method for correcting or compensating the wavelength instrumental error according to the present invention is intended to obtain the correction coefficient ($F=OD_M/OD_{ST}$) from the measured value ($OD_{ST}$) of the standard analyzer and the measured value ($OD_M$) of the measuring analyzer to be corrected, by using the standard color plate having the specific optical density value and containing the indicator dye contained in the non-reacted dry analysis element or a dye having an absorption spectrum similar to that of the indicator dye at least at the measurement wavelength range.

Only one variable is required for correction and therefore the measured value of the sample with the measuring analyzer can be corrected with one standard color plate. Excellent correction effects can be exhibited in cases that the optical density of the reagent blank is high or change of the coloring density is small. A fresh or unused slide of the dry analysis element to be used for analyses can be directly used as the correction plate (standard color plate) to be used. Accordingly, a special correction plate (standard color plate) need not be prepared separately. The standard color plate to be used for the purpose of the present invention can be manufactured in steps identical to those for the dry analysis element for use in the analysis.

Even in view of the layer coefficient L, two correction coefficients Φ, Λ as given below can be obtained from the $OD_{ST}$ and $OD_M$; $OD_{ST}$ being a value measured by the standard analyzer and $OD_M$ being a value measured by an analyzer to be corrected, $$\Phi = (OD_{ST}-L)/(OD_M-L)$$

$$\Lambda = [(OD_M-OD_{ST})/(OD_M-L)] \times L$$

regarding the layer coefficient L as a constant value.

What is claimed is:

1. A method for correcting an optical density measurement having an instrumental error, the optical density measurement to be corrected being of a sample using a first optical analyzer having an unknown instrumental error, said sample being prepared from a dry analysis element containing a first dye having an absorption spectrum and having been contacted with a sample solution containing an analyte, the method comprising the steps of:

selecting a standard color plate of a second dye selected from the group consisting of:
  a reference dye which is the same as said first dye; and
  a dye which has an absorption spectrum similar to the absorption spectrum of said first dye;
measuring and recording a standard optical density of said standard color plate using a second optical analyzer having a known instrumental error;
measuring and recording the optical density of said standard color plate using said first optical analyzer to be tested;
measuring and recording the optical density of said sample using said first optical analyzer to obtain said optical density measurement to be corrected;
calculating a corrected optical density of said prepared sample using the equation:

$$OD_C=(OD_{ST}/OD_M)\times OD_S;$$

where $OD_C$ represents said corrected optical density, $OD_{ST}$ represents said optical density of said standard color plate as measured by said second optical analyzer, $OD_M$ represents the optical density of said standard color plate as measured by said first optical analyzer, and $OD_S$ represents the optical density of said sample as measured by said first optical analyzer.

2. A method for correcting an optical density measurement having an instrumental error, the optical density measurement to be corrected being of a sample using a first optical analyzer having an unknown instrumental error, said sample being prepared from a dry analysis element containing a first dye having an absorption spectrum and having been contacted with a sample solution containing an analyte, the method comprising the steps of:

selecting a standard color plate of a second dye selected from the group consisting of:

a reference dye which is the same as said first dye;

a dye which has an absorption spectrum similar to the absorption spectrum of said first dye; and, a dye having an absorption spectrum similar to an absorption spectrum of said first dye after contact with said sample solution;

measuring and recording a standard optical density of said standard color plate using a second optical analyzer having a known instrumental error;

measuring and recording the optical density of said standard color plate using said first optical analyzer;

measuring the optical density of said sample using said first optical analyzer to obtain said optical density measurement to be corrected;

calculating an instrumental error correction coefficient gradient of wavelength using the equation:

$$\Phi=(OD_{ST}-L)/(OD_M-L);$$

where $\Phi$ represents the instrumental error correction coefficient gradient of wavelength, $OD_{ST}$ represents said optical density of said standard color plate as measured by said second optical analyzer, L represents a predetermined layer coefficient of said dry analysis element, and $OD_M$ represents the optical density of said standard color plate as measured by said first optical analyzer;

calculating an instrumental error correction coefficient intercept using the equation:

$$\Lambda=[(OD_M-OD_{ST})/(OD_M-L)]\times L;$$

where $\Lambda$ represents the instrumental error correction coefficient intercept, $OD_{ST}$ represents said optical density of said standard color plate as measured by said second optical analyzer, L represents a predetermined layer coefficient of said dry analysis element, and $OD_M$ represents the optical density of said standard color plate as measured by said first optical analyzer; and, calculating a corrected optical density of said sample using the equation:

$$OD_C=\Phi\times OD_S+\Lambda;$$

where $OD_C$ represents said corrected optical density, $\Phi$ represents the instrumental error correction coefficient gradient of wavelength, $OD_S$ represents the optical density of said sample as measured by said first optical analyzer, and $\Lambda$ represents the instrumental error coefficient intercept.

3. The method of claim 2 wherein said layer coefficient equals zero.

4. The method of claim 2 wherein said instrumental error correction coefficient intercept is a predetermined value.

5. The method of claim 4 wherein said instrumental error correction coefficient intercept equals zero.

6. The method of claim 2 wherein said standard color plate is a dry analysis element not having been in contact with a sample solution.

* * * * *